United States Patent [19]

Van Broekhoven et al.

[11] 4,421,933

[45] Dec. 20, 1983

[54] PROCESS FOR THE CO-PRODUCTION OF KETONES AND MONO-OLEFINS

[75] Inventors: Johannes A. M. Van Broekhoven; Christopher S. John, both of Amsterdam, Netherlands

[73] Assignee: Shell Oil Company, Houston, Tex.

[21] Appl. No.: 394,598

[22] Filed: Jul. 2, 1982

[51] Int. Cl.$^3$ .............................................. C07C 45/00
[52] U.S. Cl. .................................. 568/403; 568/406; 568/361; 585/275
[58] Field of Search ....................... 568/403, 406, 361; 585/275

[56] References Cited

U.S. PATENT DOCUMENTS

| 2,066,496 | 1/1937 | Taylor | 568/403 |
| 2,794,053 | 5/1957 | Altreuter et al. | 568/403 |

FOREIGN PATENT DOCUMENTS

| 817622 | 8/1959 | United Kingdom | 568/403 |
| 877143 | 9/1961 | United Kingdom | 568/403 |
| 938853 | 10/1963 | United Kingdom | 568/403 |

*Primary Examiner*—James H. Reamer
*Attorney, Agent, or Firm*—Ronald R. Reper

[57] ABSTRACT

Process for the co-production of ketones and mono-olefins from secondary alcohols and conjugated di-olefins in which dehydrogenation of the secondary alcohol and hydrogenation of the conjugated di-olefin are effected by contacting a mixture of the secondary alcohol and the conjugated di-olefin with a heterogeneous copper-containing catalytic system. The process is very useful for the co-production of methyl ethyl ketone and n-butenes from sec-butanol and butadiene at low temperatures (e.g. between 90° C. and 130° C.).

10 Claims, No Drawings

PROCESS FOR THE CO-PRODUCTION OF KETONES AND MONO-OLEFINS

BACKGROUND OF THE INVENTION

The present invention relates to a process for the co-production of ketones and mono-olefins from conjugated di-olefins and secondary alcohols. The invention relates in particular to a process for the preparation of methyl ethyl ketone (MEK) and butenes from secondary butyl alcohol (SBA) and butadiene.

It is known from U.S. Pat. No. 2,066,496, issued in 1937, that olefins may be converted in excellent yield to the corresponding saturated compounds by reacting them with an aliphatic primary or secondary monohydric alcohol containing at least two carbon atoms in the presence of a hydrogenation-dehydrogenation catalyst under conditions at which the olefin is hydrogenated while the alcohol is dehydrogenated to an aldehyde or ketone, respectively, depending on whether the alcohol is primary or secondary. Reference is made therein to a great number of metals or metal oxides which can be used as catalysts such as copper, chromium, thallium, nickel, iron and cobalt as well as the noble metals. Nickel, especially in the pyrophoric state, is the preferred catalyst. In the only example given, diisobutylene is converted into isooctane in 94% yield by reacting it with isopropyl alcohol in the presence of finely divided nickel at 250° C. in an autoclave for one hour.

When applying the teaching of the above-mentioned patent to the co-production of ketones and mono-olefins from secondary alcohols and conjugated di-olefins, the applicant learned that a supported nickel-system does not catalyze the reaction between butadiene and secondary butanol in the absence of hydrogen at temperatures up to 130° C. At that temperature oligomerization of butadiene already started to become significant. Also, various noble metal combinations did not catalyze the envisaged conversion, not even at 140° C. and pressures up to 30 bar.

Also, the conceivable use of homogeneous catalysts in combined hydrogenation/dehydrogenation reactions (in the absence of molecular hydrogen) appears to be far from attractive. It is known from a recent publication (J.C.S. Chem. Comm. 1978, 582–583) that hydrogen can be transferred from secondary alcohols to olefinic compounds using an air-sensitive, very specific organo-ruthenium catalyst, whereas closely related organo-ruthenium and organo-rhodium compounds are reported to be inactive (e.g. Bull. Chem. Soc. Japan, 1975, 48, 1585). The transfer of hydrogen from benzyl alcohol to isoprene has been reported to proceed under rather severe process conditions (12 h/200° C.), giving a rather low yield of methylbutenes using tris(triphenylphosphine) ruthenium dichloride as catalyst.

Surprisingly, it has now been found that ketones and mono-olefins can be co-produced from conjugated di-olefins and secondary alcohols under very mild process conditions when using a heterogeneous copper-containing catalyst. The hydrogenation/dehydrogenation process proceeds not only with high conversion and high selectivity, but also allows the mono-olefins produced to be used in subsequent reactions. For instance, any butene produced from butadiene can be converted by methods known per se into secondary butanol which can be used as such or as starting material for the process according to the present invention.

SUMMARY OF THE INVENTION

The present invention provides a process for the co-production of ketones and mono-olefins from secondary alcohols and conjugated di-olefins in which dehydrogenation of secondary alcohol and hydrogenation of the conjugated di-olefin are effected by contacting a feed mixture of the secondary alcohol and the conjugated di-olefin in a reaction zone with a heterogeneous copper-containing catalytic system and withdrawing a ketone and mono-olefin containing reaction product from said zone.

DESCRIPTION OF THE PREFERRED EMBODIMENTS

Conjugated di-olefins which can be suitably used in the process according to the present invention comprise 1,3-butadiene, isoprene, chloroprene, the various optionally alkyl- or chloro-substituted 1,3-pentadienes and -hexadienes as well as conjugated cyclic olefins such as 1,3-cyclohexadiene. Preference is given to the use of 1,3-butadiene as the starting material.

The conjugated di-olefins can be used as such or in admixture with mono-olefins which tend not to be reactive under the process conditions. This is of great interest since it allows the use of technical streams containing butanes, butenes and butadiene as starting material for the process according to the present invention. The use of mixtures of conjugated di-olefins and mono-olefins is also advantageous in that the mono-olefin acts as a diluent for the reactant, thus increasing the selectivity. Amounts of mono-olefins (such as butenes in 1,3-butadiene) of up to 25%v can easily be tolerated in the present process.

Secondary alcohols which can be suitably used in the process according to the present invention comprise isopropanol, sec-butanol, 2-pentanol, 3-pentanol, 3-methyl-2-butanol, 2-hexanol, 3-hexanol, 3-methyl-2-pentanol, 2-methyl-3-pentanol, 3-ethyl-2-butanol, 2-heptanol, 3-heptanol, 4-heptanol, 3-methyl-2-hexanol, 2-methyl-3-hexanol, 3-ethyl-2-pentanol, 2-ethyl-3-pentanol, 1,3-dimethyl-2-pentanol, 2,4-dimethyl-3-pentanol and cyclohexanol. Good results can be obtained using isopropanol or sec-butanol as the sec-alcohol feedstock. Also, mixtures of two or more sec-alcohols can be used, giving rise to different ketones.

The amounts of conjugated di-olefins and sec-alcohols to be used in the process according to the present invention are not critical and can vary between wide limits. Normally, volume ratios of conjugated di-olefin and sec-alcohol in the range of from 1:30 to 2:1 can be used, preference being given to the use of ratios in the range of from 1:20 to 1:10.

The process according to the present invention is carried out in the presence of a heterogeneous copper-containing catalyst. Good results can be obtained using a supported heterogeneous copper-containing catalyst. Examples of suitable supports comprise silica, alumina, magnesium oxide, zinc oxide, chromium oxide or mixtures thereof. The catalysts can be prepared by methods known in the art. For example, the inert support may be impregnated with a solution or a suspension of a copper salt, especially a copper (II)-salt which may then be converted into the corresponding oxide which is in its turn subjected to a reducing treatment, e.g. by heating for several hours in a hydrogen atmosphere. Suitable temperatures are in the range between 150° C. and 400° C.

The amount of copper on the catalyst carrier can vary widely, e.g. between 1%w and 35%w, calculated on carrier, but higher amounts are by no means excluded. Good results have been obtained using catalysts containing from 2%w to 15%w of copper calculated on carrier. If desired, the heterogeneous copper-containing catalyst to be used in the process according to the present invention may contain one or more promoters.

The process according to the present invention can be carried out under very mild process conditions. It has been found that temperatures as low as 70° C. can already be applied to convert the conjugated di-olefin almost quantitatively with a selectivity towards ketones of more than 85%. Preferred temperatures are in the range of from 90° C.–130° C. The process according to the present invention can be carried out at autogeneous or superatmospheric pressure. Good results have been obtained using a pressure in the range of from 15 to 30 bar.

If desired, the process according to the present invention may be carried out in the presence of an inert solvent. Suitable solvents comprise alkanes and cycloalkanes such as hexane, heptane and cyclohexane. Tertiary alcohols and/or ethers may also be used advantageously. Examples are tertiary butyl alcohol and methyl tertiary butyl ether. It should be noted, of course, that the secondary alcohol applied may also be used as the solvent. This will often be the case since the process is carried out preferably with a high sec-alcohol/conjugated di-olefin ratio.

The process may be carried out with the reactants being in the liquid and/or the gaseous phase. The process can be carried out batchwise, semi-continuously or continuously. Preference is given to operation of the process in a continuous manner by passing the reactants, preferably in gaseous condition, at the desired space velocity over the heterogeneous copper-containing catalyst. The product mixture obtained may then be cooled and the condensed liquid material conducted to a recovery stage wherein separation of the reaction products from each other and unreacted starting material(s), if any, may be effected by distillation, extraction or any other generally applicable technique or combination of techniques.

It may be advantageous to recycle part or all of unconverted sec-alcohol to the reactor together with any make-up sec-alcohol required. It should be noted that any co-produced mono-alkenes (e.g. butenes when butadiene is applied as the conjugated di-olefin) can be separated from the reaction mixture and either used as such or, after conversion into sec-alcohol (e.g. into sec-butanol by a hydration process), as additional feedstock for the process according to the present invention.

The present invention will now be illustrated by means of the following Examples.

EXAMPLE I

A feed containing sec-butanol and 1,3-butadiene (20/1 m/m) was passed through a tube at a temperature of 130° C. and at a pressure of 25 bar over 10 g of a catalyst comprising Cu (3%w) on γ-alumina at a space velocity of 2 l/kg cat./hr. The composition of the product mixture was analyzed using gas liquid chromatography (GLC). Over a period of 37 hours a constant butadiene conversion of 40% was observed with a constant selectivity to n-butenes (butene-1 and butene-2) of 100%. The conversion of sec-butanol into methyl ethyl ketone amounted to 2.0%m.

EXAMPLE II

A feed containing sec-butanol and 1,3-butadiene (96.1%m/3.9%m) was passed through a tube at a temperature of 80° C. and at a pressure of 25 bar over 5 g of a catalyst comprising Cu (12%) on γ-alumina at a space velocity of 2 l/kg cat./hr. The catalyst had been subjected prior to the reaction to a treatment with hydrogen at 200° C. The composition of the product mixture was analyzed using gas liquid chromatography. A constant butadiene conversion of 90% was observed with a 100% selectivity towards n-butenes. Methyl ethyl ketone had been produced in 3.9%m.

EXAMPLE III

The experiment described in the previous Example was repeated but at a temperature of 90° C. Over a period of 20 run-hours a constant butadiene conversion of 100% was monitored with a selectivity towards n-butenes of 84%. Methyl ethyl ketone had been produced in 4.7%m.

EXAMPLE IV

A feed containing sec-butanol and 1,3-butadiene (20/1 m/m) was passed through a tube at a temperature of 100° C. and at a pressure of 25 bar on 10 g of a commercially available catalyst based on Cu(II)-oxide (42%) and $Cr_2O_3$ (38%) at a space velocity of 2 l/kg cat./hr. Over a period of 65 hours the butadiene conversion remained 100%, whereas the selectivity towards n-butenes increased from 91% to 100%. The conversion of sec-butanol decreased slightly from 5.5%m to 3.8%m. Similar results can be obtained using a Cu-alumina catalyst containing also zinc or zinc oxide.

COMPARATIVE EXAMPLE A

A feed containing sec-butanol and 1,3-butadiene (92.9%m/7.1%m) was passed through a tube at a temperature increasing in time from 90° C. to 130° C. and at a pressure of 25 bar over 5 g of a catalyst comprising nickel oxide on alumina (14%w) which had been treated with hydrogen at 350° C. The experiment was carried out at a space velocity of 2 l/kg cat./hr during a period of 21 hours. No conversion of butadiene could be detected, and only traces of methyl ethyl ketone (<0.2%m) could be detected. When part of the butadiene feed was replaced with hydrogen, the product composition was analyzed after 7 run-hours. It was found that the conversion of butadiene amounted to 47%m, with a selectivity towards n-butenes of 85%, but the amount of methyl ethyl ketone had not increased at all (0.1%m).

COMPARATIVE EXAMPLE B

A feed containing isopropanol and a 1,3-butadiene, butenes and butanes stream (containing 60%v of butadiene, thus allowing an isopropanol/butadiene ratio of 4.9) was passed through a tube at a temperature of 140° C. and a pressure of 30 bar over 5 g of a catalyst containing 0.5%w of Pt and 0.25%w of Rh on a non-acidic alumina support. The amount of acetone produced did not exceed more than 0.5 mmol/hr. Also, butadiene-derived oligomers had been found.

We claim:

1. Process for the co-production of ketones and mono-olefins from secondary lower alcohols and cycloalkanols and conjugated di-olefins containing from 4 to 6 carbon atoms which comprises contacting in a reaction zone a feed mixture of said conjugated di-olefin and said secondary alcohol in a volume ratio of di-olefin to alcohol in the range from 1:30 to 2:1 at a temperature in the range from 70° to 130° C. with a supported heterogeneous copper-containing catalytic system containing between 1 and 35%w copper on carrier and withdrawing a ketone and mono-olefin-containing reaction product from said zone.

2. Process according to claim 1, wherein the feed conjugated di-olefin is 1,3-butadiene.

3. Process according to claim 1 wherein the feed secondary alcohol is selected from the group consisting of isopropanol, sec-butanol and mixtures thereof.

4. Process according to claim 1, wherein in the feed the conjugated di-olefin and the sec-alcohol are used in a volume ratio in the range of from 1:20 to 1:10.

5. Process according to claim 1 wherein said catalytic system is supported.

6. Process according to claim 1, wherein said catalytic system also contains chromium oxide or zinc oxide.

7. Process according to claim 1 wherein said catalytic system contains between 1%w and 15%w of copper, calculated on carrier.

8. Process according to claim 1, wherein said contacting is carried out at a pressure in the range of from 15 to 30 bar.

9. Process according to claim 1, wherein at least part of any unconverted sec-alcohol is separated from the reaction product and is recycled to the reaction zone together with any make-up sec-alcohol required.

10. Process according to claim 1, comprising the additional subsequent steps of (a) separating co-produced mono-alkenes from the reaction product, and (b) converting said mono-alkenes into sec-alcohols and combining the sec-alcohols from step b into the feed mixture of claim 1.

* * * * *